United States Patent [19]

Melloni et al.

[11] Patent Number: 5,272,144
[45] Date of Patent: Dec. 21, 1993

[54] ARYLOXY-, ARYLTHIO-, HETEROARYLOXY-, HETEROARYLTHIO-ALKENYLENE DERIVATIVES OF AMINES AND PHARMACEUTICAL USE

[75] Inventors: Piero Melloni, Bresso, Italy; Philippe Dostert, Paris, France; Arturo D. Torre, Gallarate; Alberto Bonsignori, Milan, both of Italy

[73] Assignee: Farmitalia Carlo Erba s.r.l., Milan, Italy

[21] Appl. No.: 499,257

[22] PCT Filed: Oct. 2, 1990

[86] PCT No.: PCT/EP89/01155
§ 371 Date: Jun. 13, 1991
§ 102(e) Date: Jun. 13, 1991

[87] PCT Pub. No.: WO90/03965
PCT Pub. Date: Apr. 19, 1990

[30] Foreign Application Priority Data
Oct. 5, 1988 [GB] United Kingdom ............... 8823405

[51] Int. Cl.$^5$ ................ A61K 31/135; A61K 31/54; C07D 279/12; C07C 217/46
[52] U.S. Cl. ............................ 514/227.5; 514/239.2; 514/317; 514/319; 514/450; 514/452; 514/466; 514/481; 514/486; 514/510; 514/524; 514/539; 514/597; 514/620; 514/630; 514/651; 544/59; 544/163; 544/174; 546/205; 546/206; 546/236; 546/240; 548/575; 548/576; 549/349; 549/350; 549/359; 549/365; 549/433; 549/443; 558/422; 560/28; 560/29; 560/42; 564/51; 564/165; 564/220; 564/347; 564/352
[58] Field of Search ............... 564/352, 353, 354, 342, 564/307, 308, 220, 221, 51, 52, 151, 165; 558/422; 514/654, 655, 651, 657, 630, 615, 597, 598, 524, 317, 236.2, 236.5, 239.2, 227.5, 428, 481, 478, 319, 450, 452, 466, 486, 520, 539, 620; 546/236, 290, 209, 206; 544/163, 174, 59; 548/570, 575, 576; 562/27; 549/349, 350, 359, 365, 433, 443; 560/28, 29, 42

[56] References Cited
U.S. PATENT DOCUMENTS

| 4,073,917 | 2/1978 | Sandberg et al. | 564/353 |
| 4,229,449 | 10/1980 | Melloni et al. | 424/248.58 |
| 4,271,160 | 6/1981 | Melloni et al. | 424/248.54 |
| 4,699,928 | 10/1987 | McDonald | 514/649 |

FOREIGN PATENT DOCUMENTS

| 2430412 | 9/1979 | France . | |
| 1110378 | 4/1968 | United Kingdom . | |
| 2060618 | 5/1981 | United Kingdom | 564/342 |
| 2087883 | 6/1982 | United Kingdom | 564/342 |

OTHER PUBLICATIONS

Chemical Abstracts, vol. 95, No. 3, Jul. 20, 1981, Abstract No. 2477w.
Chemical Abstracts, vol. 61, No. 4, Aug. 17, 1964, Abstract No. 4250g.
J. March, "Advanced Organic Chemistry," 3rd ed. pp. 638–639, John Wiley & Sons; New York (1985).

Primary Examiner—Richard L. Raymond
Attorney, Agent, or Firm—Nikaido, Marmelstein, Murray & Oram

[57] ABSTRACT

Aryloxy- and heteroaryloxy-alkylene derivatives of amines of formula

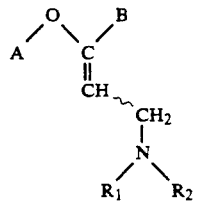

wherein each of A and B is a group of formula (i) to (iii):

(Abstract continued on next page.)

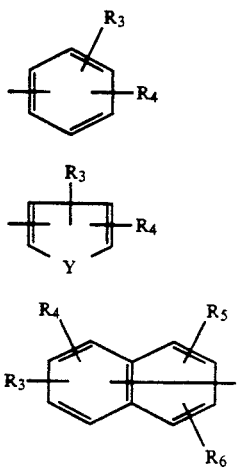

wherein
Y is —O—, —S— or —NR— in which R is hydrogen or $C_1$-$C_6$ alkyl; each of $R_3$, $R_4$, $R_5$ and $R_6$ is independently:
a) hydrogen, halogen, hydroxy, cyano or nitro;
b) $C_1$-$C_6$ alkyl unsubstituted or substituted by halogen,
c) $C_1$-$C_6$ alkoxy or $C_1$-$C_6$ alkylthio;
d) $C_1$-$C_6$ alkyl-sulfonyl;
e) a substituted amine group —$NR_7R_8$;
f) a —$COR_{12}$ group; or
g) two adjacent groups of $R_3$, $R_4$, $R_5$ and $R_6$, taken together, form a $C_1$-$C_4$ alkylenedioxy group;

each of $R_1$ and $R_2$ independently is hydrogen, $C_3$-$C_6$ alkynyl, $C_3$-$C_6$ alkenyl or $C_1$-$C_6$ alkyl unsubstituted or substituted by phenyl; or $R_1$ and $R_2$ taken together with the nitrogen atom to which they are linked, form a substituted or unsubstituted, saturated heterocyclic ring; and the pharmaceutically acceptable salts thereof; are active on the central nervous nervous system, in particular as antidepressant, antiobesity antismoking and anti-alcoholabuse agents.

8 Claims, No Drawings

ARYLOXY-, ARYLTHIO-, HETEROARYLOXY-, HETEROARYLTHIO-ALKENYLENE DERIVATIVES OF AMINES AND PHARMACEUTICAL USE

The present invention relates to aryloxy- and heteroaryloxy-alkenylene derivatives of amines, to a process for their preparation and to pharmaceutical compositions containing them.

The invention provides compounds having the following general formula (I)

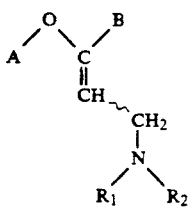

wherein
each of A and B, independently, is a group of formula (i) to (iii)

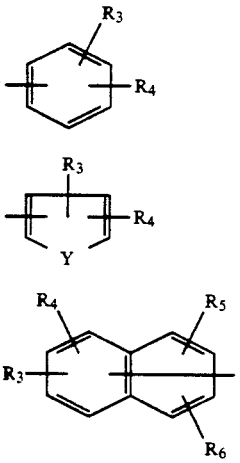

wherein
Y is —O—, —S— or —NR— in which R is hydrogen or $C_1-C_6$ alkyl;
each of $R_3$, $R_4$, $R_5$ and $R_6$ which may be the same or different, independently is;
(a) hydrogen, halogen, hydroxy, cyano or nitro;
(b) $C_1-C_6$ alkyl unsubstituted or substituted by halogen,
(c) $C_1-C_6$ alkoxy or $C_1-C_6$ alkylthio;
(d) $C_1-C_6$ alkyl-sulfonyl;
(e) a —$NR_7R_8$ group in which each of $R_7$ and $R_8$, independently, is hydrogen or $C_1-C_6$ alkyl; or one of $R_7$ and $R_8$ is hydrogen or $C_1-C_6$ alkyl and the other is a —$COR_9$ group, wherein $R_9$ is hydrogen, $C_1-C_6$ alkyl, $C_1-C_6$ alkoxy or —$NR_{10}R_{11}$ in which each of $R_{10}$ and $R_{11}$ is independently hydrogen or $C_1-C_6$ alkyl;
(f) a —$COR_{12}$ group wherein $R_{12}$ is $C_1-C_6$ alkoxy, $C_1-C_6$ alkyl or —$NR_{10}R_{11}$ wherein $R_{10}$ and $R_{11}$ are as defined above; or
(g) two adjacent of $R_3$, $R_4$, $R_5$ and $R_6$, taken together, form a $C_1-C_4$ alkylenedioxy group;
each of $R_1$ and $R_2$ independently is hydrogen, $C_3-C_6$ alkynyl, $C_3-C_6$ alkenyl; or $C_1-C_6$ alkyl unsubstituted or substituted by phenyl; or $R_1$ and $R_2$, taken together with the nitrogen atom to which they are linked, form a substituted or unsubstituted, saturated heteromonocyclic ring optionally containing a further heteroatom chosen from oxygen, sulphur and nitrogen; and the pharmaceutically acceptable salts thereof.

The invention includes within its scope all the possible isomers, stereoisomers, in particular Z and E (cis and trans) isomers and their mixtures, and the metabolites and the metabolic precursors or bio-precursors of the compounds of formula (I). In formula (I), the symbol ( ) indicates that the substituents around the carbon-carbon double bond are in the Z or E configuration or both, i.e. a mixture of Z and E isomers is present.

A halogen atom is e.g. chlorine, bromine or fluorine, preferably it is chlorine or fluorine.

The alkyl, alkenyl, alkynyl, alkylsulfonyl and alkoxy groups may be branched or straight chain groups.

A $C_1-C_6$ alkyl group is preferably a $C_1-C_4$ alkyl group, e.g. methyl, ethyl, propyl, isopropyl, butyl, sec.-butyl or tert.butyl, more preferably it is methyl or ethyl.

A $C_1-C_6$ alkyl group substituted by halogen may be a di- or tri-halo-substituted alkyl group in particular a trihalo-$C_1-C_6$ alkyl group.

A trihalo-$C_1-C_6$ alkyl group is preferably a trihalo-$C_1-C_4$ alkyl group, e.g. trichloro-$C_1-C_4$ alkyl or trifluoro-$C_1-C_4$ alkyl, more preferably it is trifluoromethyl.

A $C_3-C_6$ alkenyl group is preferably a $C_3-C_4$ alkenyl group, in particular allyl.

A $C_3-C_6$ alkynyl group is preferably a $C_3-C_4$ alkynyl group, in particular propargyl.

A $C_1-C_6$ alkoxy group is preferably a $C_1-C_4$ alkoxy group, e.g. methoxy, ethoxy, propoxy, isopropoxy, butoxy or tert.butoxy, more preferably it is methoxy or ethoxy.

A $C_1-C_6$ alkylthio group is preferably a $C_1-C_4$ alkylthio group, in particular ethylthio or methylthio, more preferably methylthio.

A $C_1-C_4$ alkylenedioxy group is in particular a $C_1-C_2$ alkylenedioxy group, preferably methylenedioxy.

A $C_1-C_6$ alkyl sulfonyl group is preferably a $C_1-C_4$ alkylsulfonyl group in particular methylsulfonyl or ethylsulfonyl.

When one or both of A and B is thienyl, it is e.g. 2-or 3-thienyl, in particular 2-thienyl.

When one or both of A and B is furyl, it is e.g. 2- or 3-furyl, in particular 2-furyl.

When one or both of A and B is pyrrolyl, it is e.g. 2-or 3-pyrrolyl, in particular 2-pyrrolyl.

When one or both of A and B is naphthyl, it is e.g. 1- or 2-naphthyl.

When one or more of $R_3$, $R_4$, $R_5$ and $R_6$ is a —$NR_7R_8$ group, as defined above under e), it is preferably:

$e_1$) amino, $C_1-C_4$ alkylamino or di ($C_1-C_4$ alkyl) amino;
$e_2$) an acetamido or propionamido group;
$e_3$) a —$NHCOOC_1-C_4$ alkyl group; or
$e_4$) an ureido or a N', N'-bis di ($C_1-C_4$ alkyl) ureido group.

When one or more of $R_3$, $R_4$, $R_5$ and $R_6$ is a —$COR_{12}$ group, as defined under f), it is preferably $f_1$) —$COC_1-C_4$ alkyl, in particular acetyl, propionyl or butyryl;

f₂) —COOC$_1$-C$_4$ alkyl, in particular methoxycarbonyl, ethoxycarbonyl or propoxycarbonyl.

f₃) —CONH$_2$, a methylamino-, ethylamino- or propylamino-carbonyl group or a dimethylamino-, diethylamino- or dipropylamino- carbonyl group.

When R$_1$ and R$_2$, taken together with the nitrogen atom to which they are linked, form a heteromonocyclic ring as defined above, it is typically a 5- or 6-membered ring.

Such a ring may be for example a ring chosen from the group including piperidine, piperazine, morpholine, thiomorpholine, pyrrolidine, which may be unsubstituted or substituted at carbon atoms or, in the case of piperazine, at a nitrogen atom by a substituent independently chosen from the group including:

C$_1$-C$_6$ alkyl; benzyl; phenyl unsubstituted or substituted by one to three substituents independently chosen from halogen, C$_1$-C$_6$ alkyl, C$_1$-C$_6$ alkoxy, trifluoromethyl and hydroxy-C$_1$-C$_6$ alkyl.

When R$_1$ and R$_2$, taken together with the nitrogen atom to which they are linked, form an heterocyclic ring as defined above, preferably it is selected from the group including:

a') unsubstituted morpholine and piperidine; and b') piperazine unsubstituted or substituted by hydroxy-C$_1$-C$_4$ alkyl, or by phenyl unsubstituted or substituted by one or two substituents independently chosen from halogen, trifluoromethyl, C$_1$-C$_4$ alkyl and C$_1$-C$_4$ alkoxy.

The pharmaceutically acceptable salts of the compounds of formula (I) include those formed with an inorganic acid, e.g. hydrochloric acid or sulphuric acid, or with an organic acid, e.g. citric, tartaric, malic, maleic, mandelic, fumaric or methanesulphonic acid.

As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein each of A and B, independently, is a group of formula (a) to (aaa)

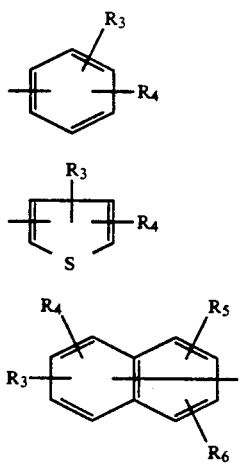

wherein each of R$_3$, R$_4$, R$_5$ and R$_6$ independently is hydrogen, halogen, hydroxy, cyano. C$_1$-C$_4$ alkylsulfonyl, nitro, C$_1$-C$_4$ alkyl, trihalo-C$_1$-C$_4$alkyl, C$_1$-C$_4$ alkoxy, a —NR$_7$R$_8$ group in which R$_7$ and R$_8$ are independently hydrogen or C$_1$-C$_4$ alkyl, or one of R$_7$ and R$_8$ is hydrogen or C$_1$-C$_4$ alkyl and the other is a —COR$_9$ group, wherein R$_9$ is hydrogen, C$_1$-C$_4$ alkyl, C$_1$-C$_4$ alkoxy or —NR$_{10}$R$_{11}$ in which each of R$_{10}$ and R$_{11}$ is hydrogen or C$_1$-C$_4$ alkyl; a —COR$_{12}$ group, wherein R$_{12}$ is C$_1$-C$_4$ alkoxy, C$_1$-C$_4$ alkyl or —NR$_{10}$R$_{11}$ in which R$_{10}$ and R$_{11}$ are as defined hereabove; or two adjacent of R$_3$, R$_4$, R$_5$ and R$_6$ taken together from a C$_1$-C$_2$ alkylenedioxy group;

each of R$_1$ and R$_2$ independently is hydrogen, C$_3$-C$_4$ alkenyl, C$_3$-C$_4$ alkynyl; or C$_1$-C$_4$ alkyl unsubstituted or substituted by phenyl; or R$_1$ and R$_2$ taken together with the nitrogen atom to which they are linked form a piperazine ring unsubstituted or N-substituted by C$_1$-C$_4$ unsubstituted or substituted by hydroxy, or a ring chosen from piperidine. morpholine, thiomorpholine, and pyrrolidine; and the pharmaceutically acceptable salts thereof.

More preferred compounds according to the present invention are the compounds of formula (I), wherein each of A and B is a group of formula (b)

wherein each of R$_3$ and R$_4$ which may be the same or different is hydrogen, halogen, C$_1$-C$_4$ alkoxy, C$_1$-C$_4$ alkyl, cyano, nitro, amino, trifluoromethyl, C$_1$-C$_4$ alkylsulfonyl, C$_2$-C$_5$ alkanoyl or two adjacent of R$_3$ and R$_4$ taken together form a methylenedioxy group;

each of R$_1$ and R$_2$, independently, is hydrogen or C$_1$-C$_4$ alkyl; and the pharmaceutically acceptable salts thereof. Preferred examples of specific compounds according to the present invention are:

α-phenoxy-α-phenyl-β-methylaminomethyl-ethylene;

α-(2-ethoxyphenoxy)-α-phenyl-β-methylaminomethyl-ethylene;

α-(2-chlorophenoxy)-α-phenyl-β-methylaminomethyl-ethylene;

α-(2,6-dichlorophenoxy)-α-phenyl-β-methylaminomethyl-ethylene;

α-(3,4-dichlorophenoxy)-α-phenyl-β-methylaminomethyl-ethylene;

α-(4-trifluoromethylphenoxy)-α-phenyl-β-methylaminomethyl-ethylene;

α-(2-nitrophenoxy)-α-phenyl-β-methylaminomethyl-ethylene,

α-(2-aminophenoxy)-α-phenyl-β-methylaminomethyl-ethylene;

α-(2-ureidophenoxy)-α-phenyl-β-methylaminomethyl-ethylene;

α-(2-thienyloxy)-α-phenyl-β-methylaminomethyl-ethylene;

α-(1-naphthyloxy)-α-phenyl-β-methylaminomethyl-ethylene;

α-(2-naphthyloxy)-α-phenyl-β-methylaminomethyl-ethylene;

α-(4-cyanophenoxy)-α-phenyl-β-methylaminomethyl-ethylene;

α-(3-chlorophenoxy)-α-phenyl-β-methylaminomethyl-ethylene;
α-(4-chlorophenoxy)-α-phenyl-β-methylaminomethyl-ethylene;
α-(2-methylphenoxy)-α-phenyl-β-methylaminomethyl-ethylene;
(E)-α-(2,6-dimethoxyphenoxy)-α-phenyl-β-methylaminomethyl-ethylene;
(E)-α-(4-nitrophenoxy)-α-phenyl-β-methylaminomethyl-ethylene;
α-(3,4-dimethoxyphenoxy)-α-phenyl-β-methylaminomethyl-ethylene;
α-(2-methoxyphenoxy)-α-phenyl-β-methylaminomethyl-ethylene;
α-(4-acetylphenoxy)-α-phenyl-β-methylaminomethyl-ethylene;
α-(3-methoxyphenoxy)-α-phenyl-β-methylaminomethyl-ethylene
α-(4-methoxyphenoxy)-α-phenyl-β-methylaminomethyl-ethylene;
α-(4-cyano-3-methoxyphenoxy)-α-phenyl-β-methylaminomethyl-ethylene;
α-(2-cyanophenoxy)-α-phenyl-β-methylaminomethyl-ethylene;
α-(3-cyanophenoxy)-α-phenyl-β-methylaminomethyl-ethylene;
α-(4-methylsulfonylphenoxy)-α-phenyl-β-methylaminomethyl-ethylene;
α-phenoxy-α-(2-thienyl)-β-methylaminomethyl-ethylene;
α-phenoxy-α-(3-chlorophenyl)-β-methylaminomethyl-ethylene;
α-phenoxy-α-(4-chlorophenyl)-β-methylaminomethyl-ethylene;
α-phenoxy-α-(2-hydroxyphenyl)-β-methylaminomethyl-ethylene;
α-phenoxy-α-(3,4-methylenedioxyphenyl)-β-methylaminomethyl-ethylene;
α-phenoxy-α-(3-methoxyphenyl)-β-methylaminomethyl-ethylene;
(E)-α-(3-hydroxyphenoxy)-α-phenyl-β-methylaminomethyl-ethylene;
α-(3,4-methylenedioxyphenoxy)-α-phenyl-β-methylaminomethyl-ethylene;
α-phenoxy-α-phenyl-β-dimethylaminomethyl-ethylene;
α-(2-ethoxyphenoxy)-α-phenyl-β-dimethylaminomethyl-ethylene;
α-(2-chlorophenoxy)-α-phenyl-β-dimethylaminomethyl-ethylene;
α-(3,4-dichlorophenoxy)-α-phenyl-β-dimethylaminomethyl-ethylene;
α-(4-trifluoromethylphenoxy)-α-phenyl-β-dimethylaminomethyl-ethylene;
α-(4-nitrophenoxy)-α-phenyl-β-dimethylaminomethyl-ethylene;
α-(2-aminophenoxy)-α-phenyl-β-dimethylaminomethyl-ethylene;
α-(2-ureidophenoxy)-α-phenyl-β-dimethylaminomethyl-ethylene;
α-(2-thienyloxy)-α-phenyl-β-dimethylaminomethyl-ethylene;
α-(1-naphthyloxy)-α-phenyl-β-dimethylaminomethyl-ethylene;
α-(2-naphthyloxy)-α-phenyl-β-dimethylaminomethyl-ethylene;
α-phenoxy-α-(2-thienyl)-β-dimethylaminomethyl-ethylene;
α-phenoxy-α-(3-chlorophenyl)-β-dimethylaminomethyl-ethylene;
α-phenoxy-α-(4-chlorophenyl)-β-dimethylaminomethyl-ethylene;
α-phenoxy-α-(3,4-methylenedioxyphenyl)-β-dimethylaminomethyl-ethylene;
α-phenoxy-α-(3-methoxyphenyl)-β-dimethylaminomethyl-ethylene;
α-(3,4-methylenedioxyphenoxy)-α-phenyl-β-dimethylaminomethyl-ethylene; and
α-phenoxy-α-phenyl-β-propargylaminomethyl-ethylene, in particular, unless specified, both as single Z and E isomers and a mixture thereof, and the pharmaceutically acceptable salts thereof.

The compounds of the invention and the salts thereof can be obtained by a process comprising:

a) reacting a compound of formula (II)

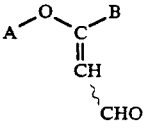

wherein

A and B are as defined above, with an amine of formula (III)

$$R_1-NH_2 \qquad (III)$$

wherein $R_1$ is as defined above, in the presence of a reducing agent, so as to obtain a compound of formula (I), wherein $R_1$ is as defined above and $R_2$ is hydrogen; or b) reducing a compound of formula (IV)

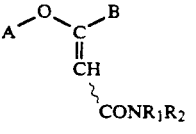

wherein

A, B, $R_1$ and $R_2$ are as defined above; or c) reacting a compound of formula (V)

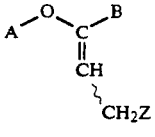

wherein

A and B are as defined above and Z is a leaving group, with an amine of formula (VI)

wherein $R_1$ and $R_2$ are as defined above; and, if desired converting a compound of formula (I) into another compound of formula (I), and/or, if desired converting a compound of formula (I) into a pharmaceutically acceptable salt thereof, and/or, if desired, converting a salt into a free compound, and/or, if desired, separating a mixture of isomers into the single isomers.

The processes a) to c) described above are analogy processes concerning reactions well known in organic chemistry.

The reaction of a compound of formula (II) with an amine of formula (III) is a reductive amination, which can be performed by treatment with a suitable reducing agent for example an alkaline boronhydride, e.g. NaBH₄ or NaBH₃CN. The reaction may be carried out in a suitable organic solvent, e.g. an aliphatic alcohol, preferably a lower alkanol, e.g. methanol or ethanol, at a temperature ranging from about 0° C. to about 20° C., in the presence of an excess of the amine of formula (II), as described e.g. in J. Med. Chem. 1980, 23, 750.

The reduction of a compound of formula (IV) may be, in general, effected by the methods usually employed for the reduction of amides, for example by treatment with LiAlH₄, AlH₃ or BH₃ in an inert anhydrous solvent, preferably an aliphatic ether, e.g. diethyl ether, or tetrahydrofuran, or a mixture of these solvents at temperatures varying from about 0° C. to about 20° C., as described e.g. in J. Med. Chem. 1981, 24, 982, or by treatment with an alkaline boronhydride, e.g. NaBH₄, in the presence of alkaline metals as described, for example, in Tetp. Lett. 1969, 4555.

When Z in a compound of formula (V) is a leaving group it is e.g. chlorine or a mesyloxy, tosyloxy or trifluoroacetate group.

The reaction of a compound of formula (V) with an amine of formula (VI) is a common nucleophile substitution well described in literature. The reaction is preferably performed in a suitable organic solvent, e.g. dimethylformamide, dimethylsulfoxide or $C_1$-$C_4$ alkanol, preferably methanol or ethanol, dioxane, tetrahydrofuran or mixture thereof, at a temperature ranging preferably from about 20° C. to about 100° C.

A compound of formula (I) may be converted, as stated above, into another compound of formula (I) by known methods. For example, a free hydroxy group may be etherified by reaction with a suitable alkyl halide in the presence of a base such as NaOH, KOH, Na₂CO₃, K₂CO₃, NaH, NaNH₂, sodium methoxide or sodium ethoxide, in a solvent selected appropriately from the group consisting, for example, of methanol, ethanol, dioxane, acetone, dimethylformamide, hexamethylphosphorotriamide, tetrahydrofuran, water and their mixtures, at a temperature rainging preferably between about 0° C. and about 150° C. Alkylation of a free amino group may be carried out according to known methods. For example a compound of formula (I) wherein one of R₁ and R₂, being as defined above, is hydrogen may be alkylated to obtain the corresponding alkyl, alkenyl, alkynyl or aralkyl derivative. The alkylation reaction may be performed, for example, by treatment with the appropriate alkyl, alkenyl, alkynyl or aralkyl halide or with a reactive ester, e.g. tosylate or mesylate, of the appropriate alcohol. The alkylation may be carried out either in the absence of solvents or in a solvent such as, e.g. an aliphatic alcohol, e.g. ethyl or methyl alcohol, a glycol, e.g. ethylenic or propylenic glycol, benzene or dimethylformamide or a mixture of these solvents in the presence of an acid acceptor such as triethylamine, an alkaline carbonate or bicarbonate or an excess of the amine, at temperatures ranging from room temperature to solvent reflux temperature according to the procedures described, e.g. in J. Org. Chem. 1938, 2, 139; Org. Synt. Coll., vol. II, 1943, 183; J. Amer. Chem. Soc., 1932, 54, 4457.

The moncalkylation may be effected, alternatively, by the methods described for example in J. Org. Chem. 1975, 40, 3453; J. Chem. Soc., 1969, 2223; J. Med. Chem. 1974, 17, 654.

Also the optional salification of a compound of formula (I) as well as the conversion of a salt into the free compound and the separation of a mixture of isomers into the single isomers may be carried out by conventional methods.

The separation of a mixture of geometric isomers may be carried out, for example, by fractional crystallization or by separation on column chromatography.

The separation of the isomers, e.g. Z and E isomers, into the single isomers, may be performed on the endproducts of formula (I), or on the intermediate products thereof.

In the processes described in the specification, when required, reactive functional groups may be protected with suitable protecting reagents, which may be removed after the reaction by known methods, which are available from the chemical literature.

The compounds of formula (II) can be obtained by reducing a compound of formula (VII)

wherein

A and B are as defined above and W is e.g. halogen, in particular chlorine, or lower alkoxy, through a suitable selective reducing agent.

In particular when W is chlorine, triterbutoxy lithium aluminium hydride can be used, analogously when W is lower alkoxy, diisobutyl aluminium hydride can be used, as described respectively e.g. in Eur. J. Med. Chem. 1984, 19, 235 or in J. Org. Chem. 1976, 41, 3512.

The reaction can be performed in organic solvents, e.g. tetrahydrofuran, diglyme or toluene, at temperatures ranging from about −60° C. to about 20° C. Alternatively the compounds of formula (II) can be obtained by reacting a compound of formula (VIII)

wherein B is as defined above, with a hydroxy derivative of formula A-OH, in which A is as defined above. The reaction can be performed in a suitable $C_1$-$C_4$ alkanol, e.g. methanol or ethanol, in the presence of a basic agent e.g. pyridine, as described e.g. in J. Chem. Soc. Perkin I, 1981, 1103, or in aprotic dipolar solvents e.g. DMF or DMSO.

The compounds of formula (IV) can be obtained e.g. by reacting a compound of formula (VII), in which W is halogen, e.g. chlorine, with an aqueous solution of an amine of formula HNR₁R₂, in which R₁ and R₂ are as defined above, at room temperature.

The same reaction may be performed by using a compound of formula (VII) wherein W is lower alkoxy, e.g. $C_1$-$C_4$ alkoxy, preferably methoxy or ethoxy, and a DMF, DMA or dioxane solution of the amine HNR₁R₂, at a temperature ranging from about 80° C. to about 100° C.

The compounds of formula (V) can be obtained by reducing a compound either of formula (II) or of formula (VII) into the corresponding alcohol and then converting the alcoholic group into a Z leaving group, as defined above. Reduction of a compound of formula (II) is preferably obtained through an alkaline borohydride, e.g. $NaBH_4$, in a lower alkanol. Similarly reduction of a compound of formula (VII) is preferably carried out by $LiAlH_4$ in diethylether or tetrahydrofuran at temperatures ranging from about $-10°$ C. to about $50°$ C. The subsequent conversion of the alcoholic group into a Z leaving group can be obtained by reaction e.g. of mesyl- or tosyl-chloride or of a reactive derivative of trifluoroacetic acid, e.g. trifluoro acetic anhydride, on the alkaline salt of the alcohol, in an aprotic dipolar solvent, such as DMF or DMSO, so as to obtain a compound of formula (V) in which Z is mesyloxy or tosyloxy or respectively trifluoroacetate. By reacting the alcohol with triphenylphosphine and $CCl_4$, as described in J. Org. Chem. 1972, 37, 1466, can analogously be obtained a compound of formula (V) in which Z is chlorine.

The compounds of formula (VII) wherein W is lower alkoxy, e.g. $C_1$-$C_4$ alkoxy, can be obtained starting from a compound of formula (IX)

    (IX)

wherein A and B are as defined above, trough reaction with a Wittig reagent, e.g. a phosphorous ylide of formula (X)

    (X)

wherein Q is $C_1$-$C_4$ alkyl or aryl e.g. phenyl and W' is lower alkoxy, according e.g. the procedure described in French Patent No. 2480283.

A compound of formula (VII) wherein W is halogen e.g. chlorine can be obtained e.g. 1) by hydrolizing the corresponding carboxylic ester of formula (VII) to the free carboxylic acid, e.g. by basic hydrolysis in an alcoholic or aqueous-alcoholic medium and then 2) heating the sodium salt of the carboxylic acid and dichloromethyl-methylether at temperatures from about $50°$ C. to about $100°$ C., as described e.g. in Ber. 1969, 92, 83.

The compounds of formula (III), (VI), (VIII), (IX) and (X) are known or may be obtained by following known methods in organic chemistry. Object of the present invention are also the compounds of formula (II)

    (II)

wherein
each of A and B, independently, is a group of formula (i) to (iii)

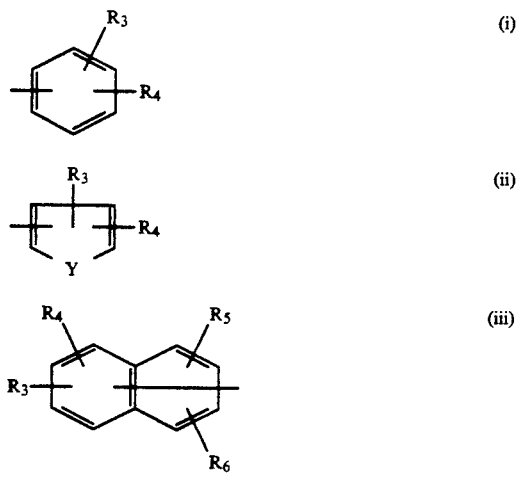

wherein
Y is —O—, —S— or —NR— in which R is hydrogen or $C_1$-$C_6$ alkyl;

each of $R_3$, $R_4$ $R_5$ and $R_6$ independently is
a) hydrogen, halogen, hydroxy, cyano or nitro;
b) $C_1$-$C_6$ alkyl unsubstituted or substituted by halogen,
c) $C_1$-$C_6$ alkoxy or $C_1$-$C_6$ alkylthio;
d) $C_1$-$C_6$alkyl-sulfonyl;
e) a —$NR_7R_8$ group in which each of $R_7$ and $R_8$, independently, is hydrogen or $C_1$-$C_6$ alkyl; or one of $R_7$ and $R_8$ is hydrogen or $C_1$-$C_6$ alkyl and the other is a —$COR_9$ group, wherein $R_9$ is hydrogen, $C_1$-$C_6$ alkyl, $C_1$-$C_6$ alkoxy or —$NR_{10}R_{11}$ in which each of $R_{10}$ and $R_{11}$ is independently hydrogen or $C_1$-$C_6$ alkyl;

f) a —$COR_{12}$ group wherein $R_{12}$ is $C_1$-$C_6$ alkoxy, $C_1$-$C_6$ alkyl or —$NR_{10}R_{11}$ wherein $R_{10}$ and $R_{11}$ are as defined above; or g) two adjacent of $R_3$, $R_4$, $R_5$ and $R_6$, taken together, form a $C_1$-$C_4$ alkylenedioxy group; and wherein, when both of A and B are as defined under (i), and A is an unsubstituted or a p-$NO_2$ substituted phenyl ring, then at least one of the remaining substituents either on the A or B ring is other than hydrogen; which are new and are useful intermediate products, according to process a) herein described.

PHARMACOLOGY

The compounds of the present invention can be used as drugs, in particular drugs active on the central nervous system, in particular as antidepressant, antiobesity, antismoking and anti-alcoholabuse agents.

The antidepressant activity was evaluated for example in mice on the basis of the prevention of reserpine-induced blepharospasm and hypothermia.

Reserpine was administered endoperitoneally at a dosage of 2.4 mg/kg, and the tested compounds were orally administered 30 minutes before the administration of reserpine. Recording of blepharospasm [evaluated in scores according to the technique described by Rubin B. et al. in J. Pharmacol., 1957, 120, 125] and measurement of body temperature (by means of a rectal thermocouple) were taken an hour, and respectively four hours after the administration of reserpine.

Some activity data of a representative group of compounds according to the present invention are shown in the following table in comparison with a reference compound.

TABLE

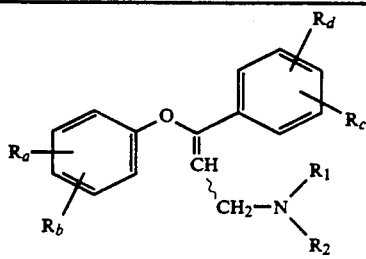

| $R_a$ | $R_b$ | $R_c$ | $R_d$ | $R_1$ | $R_2$ | ISOMER | BLEPH/ED$_{50}$ mg/kg/p · os | HYPOTH/ED$_{50}$ mg/kg/p · os |
|---|---|---|---|---|---|---|---|---|
| H | H | H | H | H | CH$_3$ | Z | 0.8 | 0.8 |
| H | H | H | H | CH$_3$ | CH$_3$ | Z | 0.5 | 1.4 |
| H | 2-Cl | H | H | H | CH$_3$ | E | 1.1 | 1.2 |
| H | 2-Cl | H | H | H | CH$_3$ | Z | 0.7 | 0.2 |
| 3-Cl | 4-Cl | H | H | H | CH$_3$ | Z | 1.2 | 1.3 |
| H | H | 3,4-OCH$_2$O— | | H | CH$_3$ | E | 1.0 | 1.4 |
| H | H | 3,4-OCH$_2$O— | | H | CH$_3$ | Z | 2.2 | 2.4 |
| IMIPRAMINE | | | | | | | 24.1 | 10.2 |

BLEPH. = Blepharospasm
HYPOTH. = Hypothermia

The compounds of the invention have been found to be active in regulating biogenic amines balance, e.g. by inhibition of reuptake of noradrenaline and/or dopamine and/or serotonine. Therefore the compounds of the present invention can be used in the alleviation, treatment and amelioration of numerous illnesses which are sensitive to changes in biogenic amines balance. By virtue of their activity the compounds of the invention can be used not only as antidepressants but also as anti-obesity, anti-smoking and anti-alcohol abuse agents.

The toxicity of the compounds of the invention is low, therefore they can be safely used in therapy. Nine hours food deprived mice were treated orally with single administration of increasing doses, then housed and normally fed. The orientative acute toxicity (LD$_{50}$) was assessed on the seventh day after the treatment.

The compounds of the invention can be administered in a variety of dosage forms, e.g. orally, in the form of tablets, capsules, sugar or film coated tablets, liquid solutions or suspensions; rectally, in the form of suppositories, parenterally, e.g. intramuscularly, or by intravenous injection or infusion. The dosage depends on the age, weight, conditions of the patient and administration route; for example the dosage adopted for oral administration to adult humans of the compound (Z)α-phenoxy-α-phenyl-β-methylaminomethyl ethylene ranges from about 2 to about 100 mg pro dose, from 1 to 5 times daily. The invention includes pharmaceutical compositions comprising a compound of the invention in association with a pharmaceutically acceptable excipient (which can be a carrier or diluent). The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervesoing mixtures; dyestuffs; sweeteners; wetting agents, such as lecithin, polysorbates, laurylsulphates; and, in general, nontoxic and pharmacologically inactive substances used in pharmaceutical formulations. Said pharmaceutical preparations may be manufactured in known manner, for example, by means of mixing, granulating, tabletting, sugar-coating, or film coating processes.

The liquid dispersions for oral administration may be e.g. syrups, emulsions and suspensions. The syrups may contain as carriers, for example, saccharose or saccharose with glycerine and/or mannitol and/or sorbitol.

The suspensions and the emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

A solution of 1.12 g ($5\times10^{-3}$ moles) of (E) 3-phenoxy-3-phenylpropenal and 2 ml ($2\times5\times10^{-2}$ moles) of 36% aqueous methylamine in 8 ml of methanol is treated with 0.19 g ($5\times10^{-3}$ moles) of NaBH$_4$ added in portions under stirring over 45 min, keeping the temperature below 10° C. The reaction is allowed to rise at room temperature and poured after 1 h in water, extracted with ethyl acetate, washed with water, dried over Na$_2$SO$_4$ and evaporated to dryness.

The residue is purified by flash chromatography (mobile phase: chloroform/methanol/30% ammonium hydroxide=190/10/1) to obtain 2.73 g of free base which is treated with 0.176 g of fumaric acid in methanol/diethylether to obtain 0.68 g of (E) α-phenoxy-α-phenyl-β-methylaminomethyl-ethylene hemifumarate m.p. 121°-124° C.

Analogously and if desired using the suitable salifying agents, the following compounds can be obtained: (Z)α-phenoxy-α-phenyl-β-methylaminomethyl-ethylene hemifumarate m.p. 140°-144° C.;

α-phenoxy-α-phenyl-β-propargyl aminomethyl-ethylene fumarate (E) isomer m.p. 131°-136° C., (Z) isomer m.p. 126°-127° C.; α-(2-ethoxyphenoxy)-α-phenyl-β-methylaminomethyl-ethylene hemifumarate (E) isomer m.p. 165°-167° C., (Z) isomer m.p. 140°-141° C.;

α-(2-chlorophenoxy)-α-phenyl-β-methylaminomethyl-ethylene hemifumarate (E) isomer m.p.152°-155° C., (Z)isomer m.p. 177°-181° C.;

α-(3-hydroxyphenoxy)-α-(phenyl)-β-methylaminomethyl-ethylene; hemifurate (E) isomer m.p. 193.5°-198° C.;

(E)-α-(2,6-dichlorophenoxy)-α-(phenyl)-β-methylaminomethyl-ethylene;

α-(3,4-dichlorophenoxy)-α-(phenyl)-β-methylaminomethyl-ethylene-hemifumarate (E) isomer m.p. 137°-141° C., (Z) isomer m.p. 159°-162° C.;

α-(3,4-methylenedioxyphenoxy)-α-(phenyl)-β-methylaminomethyl-ethylene;

α-(4-trifluoromethylphenoxy)-α-(phenyl)-β-methylaminomethyl-ethylene hemifumarate (E) isomer m.p. 144°-148° C., (Z) isomer m.p. 135°-140° C.;

α-(2-nitrophenoxy)-α-(phenyl)-β-methylaminomethyl-ethylene;

α-(2-aminophenoxy)-α-(phenyl)-β-methylaminomethyl-ethylene;

α-(2-ureido-phenoxy)-α-(phenyl)-β-methylaminomethyl-ethylene;

α-(2-thienyloxy)-α-(phenyl)-β-methylaminomethyl-ethylene;

α-(1-naphthyloxy)-α-(phenyl)-β-methylaminomethyl-ethylene;

α-(2-naphthyloxy)-α-(phenyl)-β-methylaminomethyl-ethylene;

α-(4-cyanophenoxy)-α-phenyl-β-methylaminomethyl-ethylene hemifumarate (E) isomer m.p. 159°-163° C., (Z) isomer m.p. 130°-136° C.;

α-(3-chlorophenoxy)-α-phenyl-β-methylaminomethyl-ethylene hemifumarate (E) isomer m.p. 123° C., (Z) isomer m.p. 174°-178° C.;

α-(4-chlorophenoxy)-α-phenyl-β-methylaminomethyl-ethylene hemifumarate (E) isomer m.p. 147°-150° C., (Z) isomer m.p. 136°-138° C.;

α-(2-methylphenoxy)-α-phenyl-β-methylaminomethyl-ethylene hemifumarate (E) isomer m.p. 139.5°-140° C., (Z) isomer m.p. 179°-182° C.;

α-(2,6-dimethoxyphenoxy)-α-phenyl-β-methylaminomethyl-ethylene hemifumarate (E) isomer m.p. 181.5°-184° C.;

α-(4-nitrophenoxy)-α-phenyl-β-methylaminomethyl-ethylene hemifumarate (E) isomer m.p. 153.5° C.;

α-(3,4-dimethoxyphenoxy)-α-phenyl-β-methylaminomethyl-ethylene (E) isomer (fumarate) m.p. 100°-105° C., (Z) isomer (hemifumarate) m.p. 145°-149° C.;

α-(2-methoxyphenoxy)-α-phenyl-β-methylaminomethyl-ethylene hemifumarate (E) isomer m.p. 145.5°-149.5° C., (Z) isomer m.p. 185°-191° C.;

α-(4-acetylphenoxy)-α-phenyl-β-methylaminomethyl-ethylene fumarate (E) isomer m.p. 77°-87° C., (Z) isomer m.p. 118°-122° C.;

α-(3-methoxyphenoxy)-α-phenyl-β-methylaminomethyl-ethylene;

α-(4-methoxyphenoxy)-α-phenyl-β-methylaminomethyl-ethylene;

α-(4-cyano-3-methoxy-phenoxy)-α-phenyl-β-methylaminomethyl-ethylene;

α-(2-cyanophenoxy)-α-phenyl-β-methylaminomethyl-ethylene;

α-(3-cyanophenoxy)-α-phenyl-β-methylaminomethyl-ethylene;

α-(4-methylsulfonylphenoxy)-α-phenyl-β-methylaminomethyl-ethylene;

α-phenoxy-α-(2-thienyl)-β-methylaminomethyl-ethylene;

α-phenoxy-α-(3-chlorophenyl)-β-methylaminomethyl-ethylene;

α-phenoxy-α-(4-chlorophenyl)-β-methylaminomethyl-ethylene;

α-phenoxy-α-(2-hydroxyphenyl)-β-methylaminomethyl-ethylene;

α-phenoxy-α-(3,4-methylenedioxyphenyl)-β-methylaminomethyl-ethylene hemifurate (E) isomer m.p. 145°-149° C., (Z) isomer m.p. 147°-151° C.;

α-(phenoxy-α-(3-methoxyphenyl)-β-methylaminomethylethylene hemifumarate (E) isomer m.p. 135.5°-138.5° C., (Z) isomer m.p. 144.5°-148.5° C.

EXAMPLE 2

Aluminium hydride suspension is prepared in situ by addition of a solution of 1.3 g (1×10$^{-2}$ moles) of aluminium chloride in 30 ml of ether to a stirred suspension of 1.2 g (3×10$^{-2}$ moles) of lithium aluminium hydride in 75 ml of anhydrous tetrahydrofuran and 30 ml of ether at 10°-15° C. A solution of 2.53 g (1×10$^{-2}$ moles) of (E) N-methyl-α-phenoxy-cinnamoylamide in 15 ml of anhydrous tetrahydrofuran is dropped into the suspension previously prepared. The reaction mixture is stirred at 30°-35° C. for 4 h, then is, cooled and decomposed by the addition of 3 ml of H$_2$O, 3 ml of 20% NaOH, and 5 ml of H$_2$O. The mixture is filtered and concentrated to dryness. The residue is purified by flash chromatography (mobile phase: chloroform/methanol/30% ammonium hydroxide=190:10:1) to have 1.05 g of free base which is treated with 0.25 g of fumaric acid in methanol/diethylether to obtain 0.90 g of (E) α-phenoxy-α-phenyl-β-methylaminomethyl-ethylene hemifumarate m.p. 121°-124° C.

Analogously and if desired, using the suitable salifying agents, the following compounds can be obtained: (Z)α-(phenoxy)-α-(phenyl)-β-methylaminomethyl-ethylene hemifumarate m.p. 140°-144° C.;

α-(2-ethoxyphenoxy)-α-phenyl-β-methylaminomethyl-ethylene hemifumarate (E) isomer m.p. 165°-167° C., (Z) isomer m.p. 140°-141° C.;

α-(2-chlorophenoxy)-α-phenyl-β-methylaminomethyl-ethylene hemifumarate (E) isomer m.p. 152°-155° C., (Z) isomer m.p. 177°-181° C.;

α-(3,4-dichlorophenoxy)-α-(phenyl)-β-methylaminomethylethylene hemifumarate (E) isomer m.p. 137°-141° C., (Z) isomer m.p. 159°-162° C.;

α-(3,4-methylenedioxyphenoxy)-α-(phenyl)-β-methylaminomethyl-ethylene;

α-(4-trifluoromethylphenoxy)-α-(phenyl)-β-methylaminomethyl-ethylene hemifumarate (E) isomer m.p. 144°-148° C., (Z) isomer m.p. 135°-140° C.;

α-(1-naphthyloxy)-α-(phenyl)-β methylaminomethyl-ethylene;

α-(2-naphthyloxy)-α-(phenyl)-β-methylaminomethyl-ethylene;

α-phenoxy-α-(3-chlorophenyl)-β-methylaminomethyl-ethylene;

α-phenoxy-α-(4-chlorophenyl)-β-methylaminomethyl-ethylene;

α-phenoxy-α-(3,4-methylenedioxyphenyl)-β-methylaminomethyl-ethylene; and

α-phenoxy-α-(3-methoxyphenyl)-β-methylaminomethyl-ethylene.

EXAMPLE 3

To a stirred suspension of 0.19 g ($4.77 \times 10^{-3}$ moles) of 60% NaH in 5 ml of anhydrous DMF, 1.08 g ($4.77 \times 10^{-3}$ moles) of (E) 3-phenoxy cinnamyl alcohol, in 10 ml of anhydrous DMF, is added at 10° C.

After an hour at room temperature, a solution of 0.85 g ($4.5 \times 10^{-3}$ moles) of p.toluenesulfonyl chloride in 7 ml of anhydrous DMF is added dropwise and heated at 40° C. for 4 h. The mixture is poured in water and extracted with ethyl acetate, washed with water, dried over $Na_2SO_4$ and evaporated to dryness.

The crude oil, residue (1.7 g) is used for the next step without further purification.

To a solution of 1.7 g ($4.4 \times 10^{-3}$ moles) of the crude tosylate, in 30 ml of methylene chloride, 0.90 ml ($13.2 \times 10^{-2}$ mmol) of propargylamine is added under stirring at room temperature.

After 1 hour, the reaction is heated at 50°-60° C. for 3 h. After work-up the residue obtained is purified by flash chromatography (mobile phase: ethyl acetate/hexane=100/100) to obtain 0.2 g of the free base, which is treated with 0.088 g of fumaric acid in methanol/diethylether to give 0.22 g of (E) α-phenoxy-α-phenyl-β-propargylaminomethyl-ethylene fumarate m.p. 131°-136° C.

Analogously and if desired using the suitable salifying agents, the following compounds can be obtained:

(Z) α-phenoxy-α-phenyl-β-methylaminomethyl ethylene hemifumarate m.p. 140°-144° C.;

α-(2-ethoxyphenoxy)-α-phenyl-β-methylaminomethyl-ethylene hemifumarate (E) isomer m.p. 165°-167° C., (Z) isomer m.p. 140°-141° C.;

α-(2-chlorophenoxy)-α-phenyl-β-methylaminomethyl-ethylene hemifumarate (E) isomer m.p. 152°-155° C., (Z) isomer m.p. 177°-181° C.;

α-(3-hydroxyphenoxy)-α-(phenyl)-β-methylaminomethyl-ethylene;

α-(4-hydroxyphenoxy)-α-)phenyl)-β-methylaminomethyl-ethylene;

α-(3,4-dichlorophenoxy)-α-phenyl-β-methylaminomethyl-ethylene-hemifumarate (E) isomer m.p. 137°-141° C., (Z) isomer m.p. 159°-162° C.;

α-(3,4-methylenedioxyphenoxy)-α-(phenyl)-β-methylamino-methyl-ethylene;

α-(4-trifluoromethylphenoxy)-α-(phenyl)-β-methylaminomethyl-ethylene-hemifumarate (E) isomer m.p. 144°-148° C., (Z) isomer m.p. 135°-140° C.;

α-(2-nitrophenoxy)-α-(phenyl)-β-methylaminomethyl-ethylene;

α-(2-aminophenoxy)-α-(phenyl)-β-methylaminomethyl-ethylene;

α-(2-ureido-phenoxy)-α-(phenyl)-β-methylaminomethyl-ethylene;

α-(2-thienyloxy)-α-(phenyl)-β-methylaminomethyl-ethylene;

α-(2-naphthyloxy)-α-(phenyl)-β-methylaminomethyl-ethylene;

α-(2-naphthyloxy)-α-(phenyl)-β-methylaminomethyl-ethylene;

α-phenoxy-α-(2-thienyl)-β-methylaminomethyl-ethylene;

α-phenoxy-α-(3-chlorophenyl)-β-methylaminomethyl-ethylene;

α-phenoxy-α-(4-hydroxyphenyl)-β-methylaminomethyl-ethylene; α-phenoxy-α-(2-hydroxyphenyl)-β-methylaminomethyl-ethylene;

α-phenoxy-α-(3,4-methylenedioxyphenyl)-β-methylaminomethyl-ethylene; and

α-phenoxy-α-(3-methoxyphenyl)-β-methylaminomethyl-ethylene.

EXAMPLE 4

A mixture of 3.0 g ($1.18 \times 10^{-2}$ moles) of (E) methyl-3-phenoxy cinnamate (Gazz. Chim. ital. 1981, 111, 249) and 15 ml of 36% aqueous methylamine in 35 ml of dioxane is placed in a bomb at 80° C. for 24 h.

After cooling, the solution is concentrated, poured into water and extracted with ethyl acetate, washed with water, dried over $Na_2SO_4$ and evaporated to dryness. The crude residue (E) N-methyl-α-phenoxy-cinnamoylamide is used for the next step without further purification.

Analogously, the following compounds can be obtained:

(E) N,N-dimethyl-α-phenoxy-cinnamoylamide;

(E) N-ethyl-α-phenoxy-cinnamoylamide; and (E) N,N-diethyl-α-phenoxy-cinnamoylamide.

EXAMPLE 5

A solution of 0.6 g ($2.5 \times 10^{-3}$ moles) of (Z) α-phenoxy-α-phenyl-β-methylaminomethyl-ethylene and 1.65 ml of 37% aqueous formaldehyde in 10 ml of methanol is heated under reflux for 45 min.

The solution is cooled and 0.165 g ($4.37 \times 10^{-3}$ moles) of $NaBH_4$ is added in small portions at 10° C., under stirring, over 30 min. After 1 h the solution is poured into water, extracted with ethyl acetate, washed with water, dried over $Na_2SO_4$ and evaporated to dryness to give 0.56 g of the free base which is treated 0.27 g of fumaric acid in methanol-dimethyl ether to give 0.6 g of (Z)α-phenoxy-α-phenyl-β-dimethylaminomethyl-ethylene fumarate m.p. 138°-140° C.

Analogously and if desired using the suitable salifying agents, the following compounds can be obtained: (E)α-phenoxy-α-phenyl-β-dimethylaminomethyl-ethylene fumarate m.p. 168°-170° C.

α-(2-ethoxyphenoxy)-α-phenyl-β-dimethylaminomethyl-ethylene;

α-(2-chlorophenoxy)-α-phenyl-β-dimethylaminomethyl-ethylene;

α-(3,4-dichlorophenoxy)-α-(phenyl)-β-methylaminomethyl-ethylene;

α-(3,4-methylenedioxyphenoxy)-α-(phenyl)-β-dimethylamino-methyl-ethylene;

α-(4-trifluoromethylphenoxy)-α-(phenyl)-β-dimethylamino-methyl-ethylene;

α-(2-nitrophenoxy)-α-(phenyl)-β-dimethylaminomethyl-ethylene;

α-(2-ureido-phenoxy)-α-(phenyl)-β-dimethylaminomethyl-ethylene;

α-(2-thienyloxy)-α-(phenyl)-β-dimethylaminomethyl-ethylene;

α-(1-naphthyloxy)-α-(phenyl)-β-dimethylaminomethyl-ethylene;

α-(2-naphthyloxy)-α-(phenyl)-β-dimethylaminomethyl-ethylene;

α-phenoxy-α-(2-thienyl)-β-dimethylaminomethyl-ethylene;

α-(2-aminophenoxy)-α-phenyl-β-dimethylaminomethyl-ethylene;

α-phenoxy-α-(3-chlorophenyl)-β-dimethylaminomethyl-ethylene;

α-phenoxy-α-(4-chlorophenyl)-β-dimethylaminomethyl-ethylene;

α-phenoxy-α-(3,4-methylenedioxyphenyl)-β-dimethylamino-methyl-ethylene; and

α-phenoxy-α-(3-methoxyphenyl)-β-dimethylaminomethyl-ethylene.

EXAMPLE 6

To a solution of 2.39 g ($1 \times 10^{-2}$ moles) of (E) α-phenoxy-α-phenyl-β-methylaminomethyl-ethylene in 20 ml of methanol 0.58 g ($5 \times 10^{-3}$ moles) of fumaric acid in 10 ml of methanol is added, obtaining a complete solution, which is concentrated to dryness. The residue is ground in diethylether and filtered to give 2.50 g of (E) α-phenoxy-α-phenyl-β-methylaminomethyl-ethylene hemifumarate m.p. 121°–124° C.

Analogously, the following compounds can be obtained as hemifumarate:

(Z)α-penoxy-α-phenyl-β-methylaminomethyl-ethylene m.p. 140°–144° C.

(E)α-(2-ethoxyphenoxy)-α-phenyl-β-methylaminomethyl-ethylene m.p. 165°–167° C.

(Z)α-(2-ethoxyphenoxy)-α-phenyl-β-methylaminomethyl-ethylene m.p. 140°–141° C.

(E)α-(4-trifluoromethylphenoxy)-α-(phenyl)-β-methylamino-methyl-ethylene m.p. 144°–148° C.

(Z)α-(4-trifluoromethylphenoxy)-α-(phenyl)-β-methylamino-methyl-ethylene m.p. 135°–140° C.

EXAMPLE 7

Tablets, each weighing 150 mg and containing 500 mg of the active substance can be manufactured as follows:

| Composition (for 10.000 tablets) | |
|---|---|
| (E)α-phenoxy-α-phenyl-β-methylaminomethyl-ethylene hemifumarate | 500 g |
| Lactose | 710 g |
| Corn starch | 237.5 g |
| Talc powder | 37.5 g |
| Magnesium stearate | 15 g |

(E)α-phenoxy-α-phenyl-β-methylaminomethylethylene hemifurate, lactose and a half of the corn starch are mixted; the mixture is then forced through a sieve of 0.5 mm openings. Corn starch (18 g) is suspended in warm water (180 ml).

The resulting paste is used to granulate the powder. The granules are dried, comminuted on a sieve of size 1.4 mm, then the remaining quantity of starch, talc and magnesium stearate is added, carefully mixed, and processed into tablets using punches of 8 mm diameter.

We claim:

1. A compound having the following formula (I)

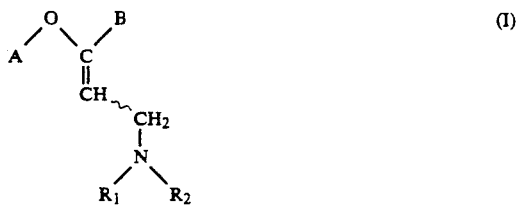

wherein
each of A and B, independently, is a group of formula (i) or (iii)

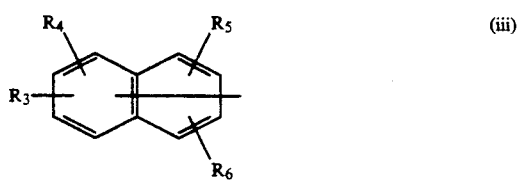

wherein
each of $R_3$, $R_4$, $R_5$ and $R_6$ which may be the same or different, independently is:

(a) hydrogen, halogen, hydroxy, cyano or nitro;

(b) $C_1$–$C_6$ alkyl unsubstituted or substituted by halogen;

(c) $C_1$–$C_6$ alkoxy or $C_1$–$C_6$ alkylthio;

(d) $C_1$–$C_6$ alkyl-sulfonyl;

(e) a —$NR_7R_8$ group in which each of $R_7$ and $R_8$, independently, is hydrogen or $C_1$–$C_6$ alkyl; or one of $R_7$ and $R_8$ is hydrogen or $C_1$–$C_6$ alkyl and the other is a —$COR_9$ group, wherein $R_9$ is hydrogen, $C_1$–$C_6$ alkyl, $C_1$–$C_6$ alkoxy or —$NR_{10}R_{11}$ in which each of $R_{10}$ and $R_{11}$ is independently hydrogen or $C_1$–$C_6$ alkyl;

(f) a —$COR_{12}$ group wherein $R_{12}$ is $C_1$–$C_6$ alkoxy, $C_1$–$C_6$ alkyl or —$NR_{10}R_{11}$ wherein $R_{10}$ and $R_{11}$ are as defined above; or (g) two adjacent of $R_3$, $R_4$, $R_5$ or $R_6$, taken together, form a $C_1$–$C_4$ alkylenedioxy group;

each of $R_1$ and $R_2$ independently is hydrogen, $C_3$–$C_6$ alkynyl, or $C_3$–$C_6$ alkenyl; or $C_1$–$C_6$ alkyl unsubstituted or substituted by phenyl; or $R_1$ and $R_2$, taken together with the nitrogen atom to which they are linked, form a substituted or unsubstituted, saturated heteromonocyclic ring optionally containing a further heteroatom chosen from oxygen, sulphur and nitrogen; and the pharmaceutically acceptable salts thereof.

2. A compound of formula (I), according to claim 1, wherein each of A and B, independently is a group of formula (a)

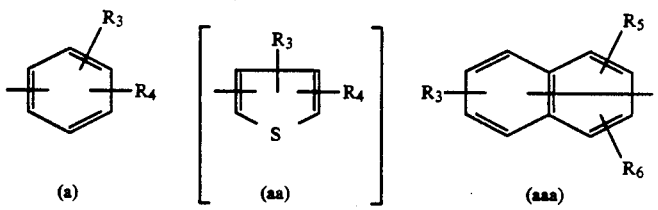

(a)  (aa)  (aaa)

wherein
each of $R_3$, $R_4$, $R_5$ and $R_6$ independently is hydrogen, halogen, hydroxy, cyano, $C_1$-$C_4$ alkylsulfonyl, nitro, $C_1$-$C_4$ alkyl, trihalo-$C_1$-$C_4$ alkyl, $C_1$-$C_4$ alkoxy, a —$NR_7R_8$ group in which $R_7$ and $R_8$ are independently hydrogen or $C_1$-$C_4$ alkyl, or one of $R_7$ and $R_8$ is hydrogen or $C_1$-$C_4$ alkyl and the other is a —$COR_9$ group, wherein $R_9$ is hydrogen, $C_1$-$C_4$ alkyl, $C_1$-$C_4$ alkoxy or —$NR_{10}R_{11}$ in which each of $R_{10}$ and $R_{11}$ is hydrogen or $C_1$-$C_4$ alkyl; a —$COR_{12}$ group, wherein $R_{12}$ is $C_1$-$C_4$ alkoxy, $C_1$-$C_4$ alkyl or —$NR_{10}R_{11}$ in which $R_{10}$ and $R_{11}$ are as defined hereabove; or two adjacent of $R_3$, $R_4$, $R_5$ and $R_6$ taken together from a $C_1$-$C_2$ alkylenedioxy group;

each of $R_1$ and $R_2$ independently is hydrogen, $C_3$-$C_4$ alkenyl, $C_3$-$C_4$ alkynyl; or $C_1$-$C_4$ alkyl unsubstituted or substituted by phenyl; or $R_1$ or $R_2$ taken together with the nitrogen atom to which they are linked form a piperazine ring unsubstituted or N-substituted by $C_1$-$C_4$ alkyl unsubstituted or substituted by hydroxy, or a ring chosen from piperidine, morpholine, thiomorpholine, and pyrrolidine; and the pharmaceutically acceptable salts thereof.

3. A compound of formula (I), according to claim 1, wherein each of A and B is a group of formula (b)

(b)

wherein each of $R_3$ and $R_4$ which may be the same or different is hydrogen, halogen, $C_1$-$C_4$ alkoxy, $C_1$-$C_4$ alkyl, cyano, nitro, amino, trifluoromethyl, $C_1$-$C_4$ alkylsulfonyl, $C_2$-$C_5$ alkanoyl or two adjacent of $R_3$ and $R_4$ taken together form a methylenedioxy group; and
each of $R_1$ and $R_2$, independently, is hydrogen or $C_1$-$C_4$ alkyl; and the pharmaceutically acceptable salts thereof.

4. A compound according to claim 1 selected from the group consisting of:

α-phenoxy-α-phenyl-β-methylaminomethyl-ethylene;
α-(2-ethoxyphenoxy)-α-phenyl-β-methylaminomethyl-ethylene;
α-(2-chlorophenoxy)-α-phenyl-β-methylaminomethyl-ethylene;
α-(2,6-dichlorophenoxy)-α-phenyl-β-methylaminomethylethylene;
α-(3,4-dichlorophenoxy)-α-phenyl-β-methylaminomethylethylene;
α-(4-trifluoromethylphenoxy)-α-phenyl-β-methylaminomethylethylene;
α-(2-nitrophenoxy)-α-phenyl-β-methylaminomethyl-ethylene;
α-(2-aminophenoxy)-α-phenyl-β-methylaminomethyl-ethylene;
α-(2-ureidophenoxy)-α-phenyl-β-methylaminomethyl-ethylene;
α-(1-naphthyloxy)-α-phenyl-β-methylaminomethyl-ethylene;
α-(2-naphthyloxy)-α-phenyl-β-methylaminomethyl-ethylene;
α-(4-cyanophenoxy)-α-phenyl-β-methylaminomethyl-ethylene;
α-(3-chlorophenoxy)-α-phenyl-β-methylaminomethyl-ethylene;
α-(4-chlorophenoxy)-α-phenyl-β-methylaminomethyl-ethylene;
α-(2-methylphenoxy)-α-phenyl-β-methylaminomethyl-ethylene;
(E)-α-(2,6-dimethoxyphenoxy)-α-phenyl-β-methylaminomethylethylene;
(E)-α-(4-nitrophenoxy)-α-phenyl-β-methylaminomethylethylene;
α-(3,4-dimethoxyphenoxy)-α-phenyl-β-methylaminomethylethylene;
α-(2-methoxyphenoxy)-α-phenyl-β-methylaminomethyl-ethylene;
α-(4-acetylphenoxy)-α-phenyl-β-methylaminomethyl-ethylene;
α-(3-methoxyphenoxy)-α-phenyl-β-methylaminomethyl-ethylene;
α-(4-methoxyphenoxy)-α-phenyl-β-methylaminomethyl-ethylene;
α-(4-cyano-3-methoxyphenoxy)-α-phenyl-β-methylaminomethylethylene;
α-(2-cyanophenoxy)-α-phenyl-β-methylaminomethyl-ethylene;
α-(3-cyanophenoxy)-α-phenyl-β-methylaminomethyl-ethylene;
α-(4-methylsulfonylphenoxy)-α-phenyl-β-methylaminomethylethylene;
α-phenoxy-α-(3-chlorophenyl)-β-methylaminomethyl-ethylene;
α-phenoxy-α-(4-chlorophenyl)-β-methylaminomethyl-ethylene;
α-phenoxy-α-(2-hydroxyphenyl)-β-methylaminomethyl-ethylene;
α-phenoxy-α-(3,4-methylenedioxyphenyl)-β-methylaminomethyl-ethylene;
α-phenoxy-α-(3-methoxyphenyl)-β-methylaminomethyl-ethylene;
(E)-α-(3-hydroxyphenoxy)-α-phenyl-β-methylaminomethyl-ethylene;
α-(3,4-methylenedioxyphenoxy)-α-phenyl-β-methylaminomethyl-ethylene;
α-phenoxy-α-phenyl-β-dimethylaminomethyl-ethylene;
α-(2-ethoxyphenoxy)-α-phenyl-β-dimethylaminomethyl-ethylene;
α-(2-chlorophenoxy)-α-phenyl-β-dimethylaminomethyl-ethylene;

α-(3,4-dichlorophenoxy)-α-phenyl-β-dimethylaminomethyl-ethylene;

α-(4-trifluoromethylphenoxy)-α-phenyl-β-dimethylaminomentyl-ethylene;

α-(4-nitrophenoxy)-α-phenyl-β-dimethylaminomethyl-ethylene;

α-(2-aminophenoxy)-α-phenyl-β-dimethylaminomethyl-ethylene;

α-(2-ureidophenoxy)-α-phenyl-β-dimethylaminomethyl-ethylene;

α-(1-naphthyloxy)-α-phenyl-β-dimethylaminomethyl-ethylene;

α-(2-naphthyloxy)-α-phenyl-β-dimethylaminomethyl-ethylene;

α-phenoxy-α-(3-chlorophenyl)-β-dimethylaminomethyl-ethylene;

α-phenoxy-α-(4-chlorophenyl)-β-dimethylaminomethyl-ethylene;

α-phenoxy-α-(3,4-methylenedioxyphenyl)-β-dimethylaminomethyl-ethylene;

α-phenoxy-α-(3-methoxyphenyl)-β-dimethylaminomethyl-ethylene;

α-(3,4-methyenedioxyphenoxy)-α-phenyl-β-dimethylaminomethyl-ethylene; and

α-phenoxy-α-phenyl-β-propargylaminomethyl-ethylene. unless specified, both as single Z and E isomers and a mixture thereof; and the pharmaceutically acceptable salts thereof.

5. A pharmaceutical composition containing a suitable carrier and/or diluent and, as an active principle, a compound of formula (I) according to claim 1, or a pharmaceutically acceptable salt thereof.

6. A method of treating a human suffering from depression, of stopping a human from smoking or of stopping a human from abusing alcohol, which method comprises administering to the said human an effective amount of a compound of formula (I) or pharmaceutically acceptable salt thereof as defined in claim 1.

7. A method of inhibiting the reuptake of biogenic amines selected from the group consisting of noradrenaline, dopamine and serotonin in a human, comprising administering to said human an effective amount of a compound of the formula (I)

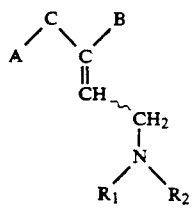

wherein
each of A and B, independently, is a group of formula (i) or (iii)

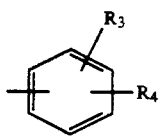

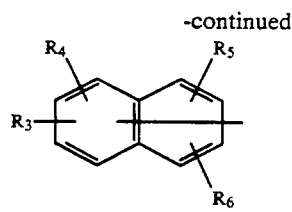

wherein
each of $R_3$, $R_4$, $R_5$ and $R_6$ which may be the same or different, independently is:

(a) hydrogen, halogen, hydroxy, cyano or nitro;

(b) $C_1-C_6$ alkyl unsubstituted or substituted by halogen;

(c) $C_1-C_6$ alkoxy or $C_1-C_6$ alkylthio;

(d) $C_1-C_6$ alkyl-sulfonyl;

(e) a —$NR_7R_8$ group in which each of $R_7$ and $R_8$, independently, is hydrogen or $C_1-C_6$ alkyl; or one of $R_7$ and $R_8$ is hydrogen or $C_1-C_6$ alkyl and the other is a —$COR_9$ group, wherein $R_9$ is hydrogen, $C_1-C_6$ alkyl, $C_1-C_6$ alkoxy or —$NR_{10}R_{11}$ in which each of $R_{10}$ and $R_{11}$ is independently hydrogen or $C_1-C_6$ alkyl;

(f) a —$COR_{12}$ group wherein $R_{12}$ is $C_1-C_6$ alkoxy, $C_1-C_6$ alkyl or —$NR_{10}R_{11}$ wherein $R_{10}$ and $R_{11}$ are as defined above; or (g) two adjacent of $R_3$, $R_4$, $R_5$ or $R_6$, taken together, form a $C_1-C_4$ alkylenedioxy group;

each of $R_1$ and $R_2$ independently is hydrogen, $C_3-C_6$ alkynyl, or $C_3-C_6$ alkenyl; or $C_1-C_6$ alkyl unsubstituted or substituted by phenyl; or $R_1$ and $R_2$, taken together with the nitrogen atom to which they are linked, form a substituted or unsubstituted, saturated heteromonocyclic ring optionally containing a further heteroatom chosen from oxygen, sulphur and nitrogen; and the pharmaceutically acceptable salts thereof.

8. A method of controlling obesity in a human, comprising administering to said human an effective amount of a compound of the formula (I)

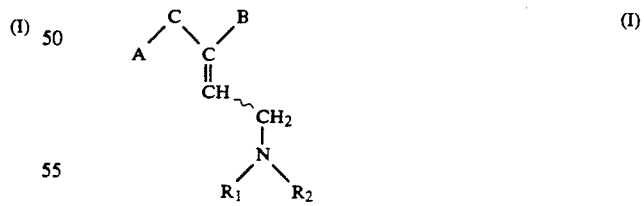

wherein
each of A and B, independently, is a group of formula (i) or (iii)

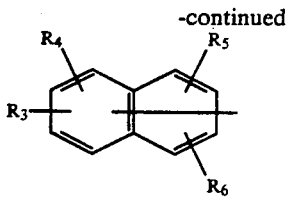

(iii)

wherein
each of $R_3$, $R_4$, $R_5$ and $R_6$ which may be the same or different, independently is:
(a) hydrogen, halogen, hydroxy, cyano or nitro;
(b) $C_1$-$C_6$ alkyl unsubstituted or substituted by halogen;
(c) $C_1$-$C_6$ alkoxy or $C_1$-$C_6$ alkylthio;
(d) $C_1$-$C_6$ alkyl-sulfonyl;
(e) a —$NR_7R_8$ group in which each of $R_7$ and $R_8$, independently, is hydrogen or $C_1$-$C_6$ alkyl; or one of $R_7$ and $R_8$ is hydrogen or $C_1$-$C_6$ alkyl and the other is a —$COR_9$ group, wherein $R_9$ is hydrogen, $C_1$-$C_6$ alkyl, $C_1$-$C_6$ alkoxy or —$NR_{10}R_{11}$ in which each of $R_{10}$ and $R_{11}$ is independently hydrogen or $C_1$-$C_6$ alkyl;
(f) a —$COR_{12}$ group wherein $R_{12}$ is $C_1$-$C_6$ alkoxy, $C_1$-$C_6$ alkyl or —$NR_{10}R_{11}$ wherein $R_{10}$ and $R_{11}$ are as defined above; or
(g) two adjacent of $R_3$, $R_4$, $R_5$ or $R_6$, taken together, form a $C_1$-$C_4$ alkylenedioxy group;
each of $R_1$ and $R_2$ independently is hydrogen, $C_3$-$C_6$ alkynyl, or $C_3$-$C_6$ alkenyl; or $C_1$-$C_6$ alkyl unsubstituted or substituted by phenyl; or
$R_1$ and $R_2$, taken together with the nitrogen atom to which they are linked, form a substituted or unsubstituted, saturated heteromonocyclic ring optionally containing a further heteroatom chosen from oxygen, sulphur and nitrogen; and the pharmaceutically acceptable salts thereof.

* * * * *

UNITED STATES PATENT AND TRADEMARK OFFICE
CERTIFICATE OF CORRECTION

PATENT NO.   : 5,272,144
DATED        : December 21, 1993
INVENTOR(S)  : Piero MELLONI et al It is certified that error appears in the above-indentified patent and that said Letters Patent is hereby corrected as shown below:

In Claim 2, Column 18, Line 68, after "formula (a)" insert -- or (aaa); --.

In Claim 2, Column 19, Lines 1 through 10, delete:

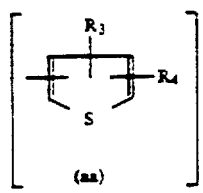

In Claim 4, Column 21, Line 25, change "(3,4-methyenedioxyphenoxy) to -- (3,4-methylenedioxyphenoxy) --.

In Claim 7, Column 21, Lines 49 through 56, Figure (I), change: 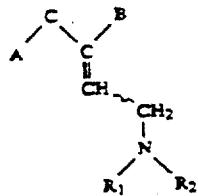 to: 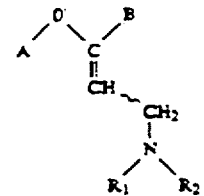

UNITED STATES PATENT AND TRADEMARK OFFICE
CERTIFICATE OF CORRECTION

PATENT NO. : 5,272,144
DATED : December 21, 1993
INVENTOR(S) : Piero MELLONI et al It is certified that error appears in the above-indentified patent and that said Letters Patent is hereby corrected as shown below:

In Claim 8, Column 22, Lines 46 through 56, Figure (I), change: 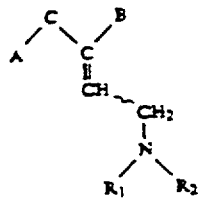 to: 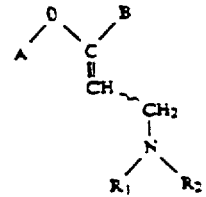

Signed and Sealed this

Nineteenth Day of March, 1996

BRUCE LEHMAN

*Attest:*

*Attesting Officer*   *Commissioner of Patents and Trademarks*